United States Patent [19]
Askelöf et al.

[11] Patent Number: 5,935,838
[45] Date of Patent: Aug. 10, 1999

[54] METHOD OF CULTIVATING BACTERIA PROTEINS THAT ARE EXPRESSED IN A TEMPERATURE REGULATED MANNER

[75] Inventors: Per Askelöf, Sollentuna; Nils Carlin, Vällingby; Bo Nilsson, Lidingö; Agneta Paulsson, Nyköping, all of Sweden

[73] Assignee: SBL Vaccin AB, Stockholm, Sweden

[21] Appl. No.: 08/750,509

[22] PCT Filed: Jun. 1, 1995

[86] PCT No.: PCT/SE95/00628

§ 371 Date: Apr. 21, 1997

§ 102(e) Date: Apr. 21, 1997

[87] PCT Pub. No.: WO95/33825

PCT Pub. Date: Dec. 14, 1995

[30] Foreign Application Priority Data

Jun. 3, 1994 [SE] Sweden .................................. 9401921

[51] Int. Cl.⁶ ............................. C12N 1/12; C12N 1/20; C12N 15/00; C12P 21/04
[52] U.S. Cl. ....................... 435/252.1; 435/71.1; 435/91; 435/170; 435/69.1; 435/172.3; 435/252.3; 435/232; 435/320.1; 435/69.3
[58] Field of Search ............................... 435/252.1, 71.1, 435/91, 170, 69.1, 172.3, 252.3, 232, 320.1, 69.3

[56] References Cited

U.S. PATENT DOCUMENTS 5,043,277  8/1991  Fukuhara et al. .
5,322,786  6/1994  Fukuhara et al. .

FOREIGN PATENT DOCUMENTS

| 0279665 A2 | 8/1988 | European Pat. Off. . |
| 279665 | 8/1988 | European Pat. Off. . |
| 0467676 A2 | 1/1992 | European Pat. Off. . |
| 467676 | 1/1992 | European Pat. Off. . |
| 92/14487 | 9/1992 | WIPO . |
| WO 9214487 A1 | 9/1992 | WIPO . |

OTHER PUBLICATIONS

Gustafsson et al, J. Clin. Microbiol, 26/10:2077–2082, Oct., 1988.
Carlin, et al, Inf. & Imm. 55/6: 1412–1420, Jun. 1987.
Betenbaugh et al, Biotechnol & Bioengin 36: 124–134, 1990.
J. Clin. Microbiol. 23(3):586–591, Mar. 1986.
J. Clin. Microbiol. 28(10):2264–2268, OCt. 1990.

Primary Examiner—Nita Minnifield
Attorney, Agent, or Firm—Darby & Darby

[57] ABSTRACT

A method of cultivating bacteria having genes in plasmids which code for surface or membrane bound antigens or other proteins and which are expressed in a temperature regulated manner for the production of desired bacterial products, is disclosed. The bacteria are first cultivated in a culture medium to an inoculum under such temperature conditions that the bacteria retain their plasmids and no expression occurs, e.g. 20° C., and then in a culture medium under such temperature conditions that expression occurs and before the bacteria lose their plasmids they are harvested, and the desired product is isolated.

12 Claims, No Drawings

METHOD OF CULTIVATING BACTERIA PROTEINS THAT ARE EXPRESSED IN A TEMPERATURE REGULATED MANNER

The present invention relates to a method of cultivating bacteria. More precisely, the method is concerned with cultivating bacteria having genes in plasmids which code for surface or membrane bound antigens or other proteins and which are expressed in a temperature regulated manner for the production of desired bacterial products.

BACKGROUND

Bacteria and viruses often express on or within their membrane, proteins which in a certain environment function as a support for the organism to associate in a specific way or adhere to a surface. Such a surface may be the inner wall of the gastro-intestinal tract, the oesophagus or any other biological surface or membrane in a human or animal body, where an organism may find an optimal environment for growth. Membrane proteins of this kind are often named colonization-factor-antigens (CFA) or fimbriae. In the literature, other words such as pili, hemagglutinins, filamentous or fibrillar proteins are used for the same kind of substances. For convenience, "CFA" will be used herein to cover all these kinds of membrane proteins which also may have an antigenic character.

A number of bacteria which are of medical interest have been shown to produce CFAs associated with their membrane. Among these, the ones which are most important for humans, are organisms which colonize the human gastro-intestinal tract and the respiratory airways. Examples of organisms which colonize the gastro-intestinal tract are enterotoxigenic *Escherichia coli, Vibrio cholerae, Helicobacter pylor*, Campylobacter, Shigellae, Salmonellae and Yersinia.

Of particular medical interest is the enterotoxigenic *Escherichia coli* (ETEC), since it is one of the major causes of diarrhea among children in the developing countries and accounts for more than 1 billion diarrhea episodes and at least one million deaths per year, primarily among children. In the same way, *Vibrio cholerae* and Campylobacter cause diarrhea among people in the developing countries. ETEC and Campylobacter are also the major cause of diarrhea among travellers to these regions. *Helicobacter pylori* has recently become important due to its connection with stomach ulcers.

For most of these organisms the production of their CFAs is controlled by various factors in the environment, which in turn may activate regulatory genes in the plasmid DNA.

Thus, for a bacterium which has its natural growth environment in the human intestine it is advantageous to optimize its growth and possibility of survival to conditions in the intestine. In other words, there is an optimal strategy of survival which implies the production of adhesive proteins in the environment where there are suitable conditions for survival.

As is known from the literature, one such parameter that activates regulatory plasmid genes is the temperature, implying that the production of CFAs in a number of bacteria is temperature regulated. Several human pathogenic organisms have been shown to produce CFAs at temperatures above room temperature only, and not at room temperature. Some of these organisms are of specific commercial interest, since it has been shown that it is possible to produce oral vaccines against these organisms or bacteria.

In WO 92/14487 a method for production and use of an oral ETEC vaccine is disclosed. The ETEC bacteria are grown at 37° C. from agar plates to liquid medium in order to obtain commercial quantities of the ETEC bacteria with CFAs and their sub-components (CS-antigens). These subsequently formalin killed bacteria may then be used as an oral vaccine against the ETEC bacteria. The CFA and CS antigens will thus function as antigens in the immunological processing that will take place in the intestine.

In the scaling up of the production of ETEC bacteria having CFAs it was surprisingly found that the bacteria lost their ability to produce CFAs more and more for each new generation. In the studying of the reason for this, it was noticed that the loss of the ability of the bacteria to produce CFAs at temperatures above room temperature was accompanied by a loss of the regulatory gene localized in a plasmid in the bacteria.

DESCRIPTION OF THE INVENTION

The present invention is directed to a method of cultivating bacteria having genes in plasmids which code for surface or membrane bound antigens or other proteins and which are expressed in a temperature regulated manner for the production of desired bacterial products, wherein said bacteria are first cultivated in a culture medium to an inoculum under such temperature conditions that the bacteria retain their plasmids and no expression occurs, and then said inoculum is further cultivated in a culture medium under such temperature conditions that expression occurs and before the bacteria lose their plasmids they are harvested, and after that the desired product is isolated.

Examples of genes in plasmids which code for other proteins and which are expressed in a temperature regulated manner for the production of desired bacterial products are recombinant genes in plasmids which retain their temperature regulated expression and produce desired protein products.

In a preferred embodiment, the first cultivation to an inoculum is conducted at room temperature and the further cultivation is conducted at the body temperature of a mammal.

In another preferred embodiment the room temperature is approximately 20° C. and the body temperature of a mammal is 34–39° C.

In yet another preferred embodiment, the first cultivation to an inoculum is conducted in two steps, first on a culture plate and then in a liquid culture medium.

In still another preferred embodiment of the invention, the further cultivation is conducted in a liquid culture medium.

These preferred embodiments of the invention make it possible to cultivate bacteria having genes in plasmids which code for surface or membrane bound antigens or other proteins and which are expressed in a temperature regulated manner in large scale industrial fermentors for large scale production of desired bacterial products.

In an embodiment of the invention the cultivated bacteria are *Escherichia coli* expressing at least one type of colonization factor antigens selected from the group consisting of CFA/I, CS1, CS2, CS3, CS4, CS5 and CS6.

In such cultivation, the desired bacterial product may either be the *E. coli* carrying at least one of the colonization factor antigens CFA/I, CS1, CS2, CS3, CS4, CS5 and CS6 or such colonization factor antigens isolated from the bacteria.

EXAMPLES

In the following examples CFA medium has been used as culture medium. The composition of the liquid CFA medium is as follows: Casamino Acids 1% (w/v), Yeast extract 0.078% (w/v), MgSO$_4$ 0.4 mM, MnCl$_2$ 0.04 mM, H$_2$O deionized, pH 7.4. As culture plates, CFA agar plates have been used. These include CFA medium with 20 g/liter added.

Example 1.

An ETEC stain expressing CS2+CS3 antigens was taken from −70° C. and evaluated regarding expression of the membrane components as follows.

CFA agar plates were inoculated with the strain CS2+CS3 and incubated at 20° C. or 37° C. for 24 hours. The bacteria were harvested from the plates and samples containing 40×10$^6$ bacteria each were further inoculated in a 800 ml (CFA medium) shake culture at 20° C. or 37° C. for another 24 hours. At 70 hours a sample of 4.5 ml was taken from the 20° C. culture and was further cultivated at 37° C. in a 800 ml shake culture (CFA medium). At various intervals the expression of CS2 was analyzed with an ELISA technique using a monoclonal antibody which has been shown to have specificity for the CS2 antigen. All ELISA results have been adjusted to standardized amount of bacteria as measured by their optical density. The results as measured in ELISA-arbitrary units are presented in the Table 1.

TABLE 1

| Time (hours) | ELISA units at 20° C. | ELISA units at 20° C. + 37° C. | ELISA units at 37° C. |
| --- | --- | --- | --- |
| 0 | 8 | 8 | 8 |
| 24 | 8 | 8 | 643 |
| 48 | 8 | 8 | 762 |
| 54 | 8 | 8 | 897 |
| 70 | 25 | 25 | 1127 |
| 74 | 58 | 361 | 814 |
| 79 | 64 | 736 | 537 |
| 96 | 85 | 850 | 214 |

Example 2.

Under the same conditions as in Example 1, ETEC bacteria with CS4 antigen were grown in liquid CFA medium. After the sampling at 31 hours, the temperature was raised to 37° C.

The results as measured in ELISA-arbitrary units can be seen in Table 2.

TABLE 2

| Time (hours) | ELISA units at 20° C. | ELISA units at 20° C. + 37° C. |
| --- | --- | --- |
| 0 | 0 | 0 |
| 24 | 0 | 0 |
| 26 | 0 | 0 |
| 29 | 0 | 0 |
| 31 | 0 | 0 |
| 48 | 0 | 8 |
| 52 | 1 | 9 |
| 54 | 1 | 10 |

Example 3.

Under the same conditions as in Example 1, ETEC bacteria with CS5 antigen were grown in liquid CFA medium. After the sampling at 31 hours, the temperature was raised to 37° C.

The result as measured in ELISA-arbitrary units can be seen in Table 3.

TABLE 3

| Time (hours) | ELISA units at 20° C. | ELISA units at 20° C. + 37° C. |
| --- | --- | --- |
| 0 | 0 | 0 |
| 24 | 0 | 0 |
| 26 | 0 | 0 |
| 29 | 0 | 0 |
| 31 | 0 | 0 |
| 48 | 1 | 5 |
| 52 | 1 | 8 |
| 54 | 1 | 8 |

Example 4.

A culture of ETEC bacteria expressing the antigen CS1 was grown overnight in liquid CFA medium on a shaker at 37° C. Colonies were plated on CFA agar and incubated at 37° C. overnight. The following day, colonies expressing CS1 fimbriae were detected by a colony blot method using a CS1 specific mouse monoclonal antibody as second antibody. Immunoblots were developed by a nitro blue tetrasodium salt stain. Individual CS1 fimbriae positive and negative colonies were picked and cultivated, spread on CFA agar plates as described above.

This time each plate was probed with one filter for the CS1 specific monoclonal antibody as described above and also with one filter that was used for colony hybridization with one of two radioactivity labelled (32P) probes. One probe specific for the structural gene of CS1 (cooA) and one probe specific for the regulatory RNS protein (rns).

Postive colonies: All colonies scored positive with the antibody assay were also scored positive with the rns probe and CS1 probe.

Negative colonies: No colonies scored negative with antibody had any reaction with the rns probe, a few negative colonies had lost also their reactivity with the CS1 probe but most of them had retained their CS1 structural genes.

In conclusion, there is a concomitant loss of CS1 antibody reactivity (expression of CS1 fimbriae) and loss of reactivity with the rns probe (loss of the plasmid encoding the rns gene).

We claim:

1. A method of cultivating bacteria having genes in plasmids which code for surface or membrane bound antigens or other proteins and which are expressed in a temperature regulated manner for the production of desired bacterial products wherein said plasmids are retained during cultivation comprising:

(a) inoculating and cultivating said bacteria in a culture medium at room temperature so that the bacteria retain their plasmids and no expression occurs;

(b) further cultivating said culture medium of step (a) in a culture medium at 34–39° C. so that expression of said surface or membrane bound antigens or other proteins occurs;

(c) harvesting said bacteria before they lose their plasmids; and (d) isolating the desired bacterial products, said products being the surface or membrane bound antigens or other proteins, or the bacteria having genes in plasmids which code for such surface or membrane bound antigens or other protein.

2. The method of claim 1, wherein said room temperature is approximately 20° C.

3. The method of claim 1, wherein said cultivating at room temperature of step (a) is conducted in two steps, first on a culture plate and then in a liquid culture medium.

4. The method of claim 1, wherein the further cultivation is conducted in a liquid culture medium.

5. The method of claim 1, wherein said bacteria are *Escherichia coli* expressing at least one type of colonization factor antigens selected from the group consisting of CFA/l, CS1, CS2, CS3, CS4, CS5 and CS6.

6. The method of claim 1, wherein said desired bacterial product is at least one of the colonization factor antigens selected from the group consisting of CFA/I, CS1, CS2, CS3, CS4, CS5 and CS6.

7. The method of claim 2, wherein said cultivating at room temperature of step (a) is conducted in two steps, first on a culture plate and then in a liquid culture.

8. The method of claim 2, wherein said further cultivating is conducted in a liquid culture medium.

9. The method of claim 3, wherein said further cultivating is conducted in a liquid culture medium.

10. The method of claim 2, wherein said bacteria are *Escherichia coli* expressing at least one type of colonization factor antigens selected from the group consisting of CFA/l, CS1, CS2, CS3, CS5 and CS6.

11. The method of claim 3, wherein said bacteria are *Escherichia coli* expressing at least one type of colonization factor antigens selected from the group consisting of CFA/l, CS1, CS2, CS3, CS5 and CS6.

12. The method of claim 4, wherein said bacteria are *Escherichia coli* expressing at least one type of colonization factor antigens selected from the group consisting of CFA/l, CS1, CS2, CS3, CS5 and CS6.

* * * * *

UNITED STATES PATENT AND TRADEMARK OFFICE
CERTIFICATE OF CORRECTION

PATENT NO. : 5,935,838
DATED : April 10, 1999
INVENTOR(S) : Per Askelof et al.

It is certified that error appears in the above-identified patent and that said Letters Patent is hereby corrected as shown below:

Title page, [75] Inventors city of residence, change "VALLINGBY SWEDEN" to --HASSELBY, SWEDEN--.

Signed and Sealed this

Ninth Day of May, 2000

Attest:

Q. TODD DICKINSON

Attesting Officer

Director of Patents and Trademarks